United States Patent [19]

Cosman

[11] Patent Number: 4,618,978
[45] Date of Patent: Oct. 21, 1986

[54] MEANS FOR LOCALIZING TARGET COORDINATES IN A BODY RELATIVE TO A GUIDANCE SYSTEM REFERENCE FRAME IN ANY ARBITRARY PLANE AS VIEWED BY A TOMOGRAPHIC IMAGE THROUGH THE BODY

[76] Inventor: Eric R. Cosman, 872 Concord Ave., Belmont, Mass. 02178

[21] Appl. No.: 544,090

[22] Filed: Oct. 21, 1983

[51] Int. Cl.[4] .............................................. H05G 1/28
[52] U.S. Cl. ................................ 378/164; 128/303 B; 378/162
[58] Field of Search .......................... 378/20, 162–164, 378/205; 128/303 B

[56] References Cited

U.S. PATENT DOCUMENTS

| | | | |
|---|---|---|---|
| 4,319,136 | 3/1982 | Jinkins | 378/163 |
| 4,341,220 | 7/1982 | Perry | 378/162 |
| 4,400,819 | 8/1983 | Bens et al. | 378/20 |

Primary Examiner—Bruce C. Anderson
Assistant Examiner—Charles Wieland
Attorney, Agent, or Firm—Richard J. Birch

[57] ABSTRACT

A localizer system is described which enables determination of the coordinates of a target located inside the human body and visualized on a tomographic scan image for essentially any arbitrary scan plane through the body. It involves a means of fixing a frame in a known relationship to the body and placing the localizer system in a fixed position relative to the frame. There is an axial axis defined for the localizer, and there are both parallel and transverse (perpendicular) rod elements as well as diagonal rod elements on the localizer. These appear as spot images on the scan plane image and are sufficient in number and location to enable accurate calculation of a target image on the scan and determination of the target coordinates in space relative to the localizer. This applies to plane scan cuts which are substantially parallel or perpendicular to the localizer axis.

1 Claim, 15 Drawing Figures

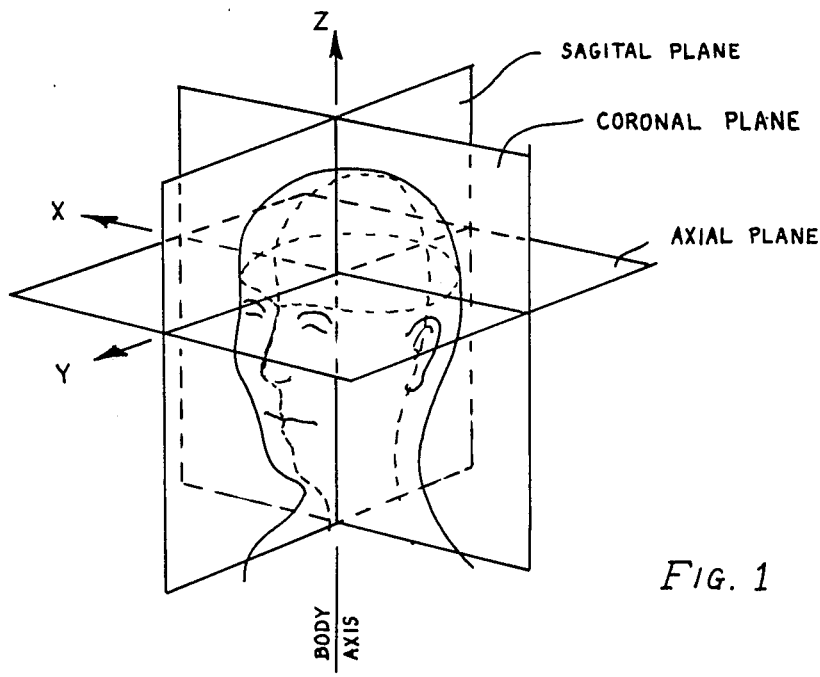
FIG. 1
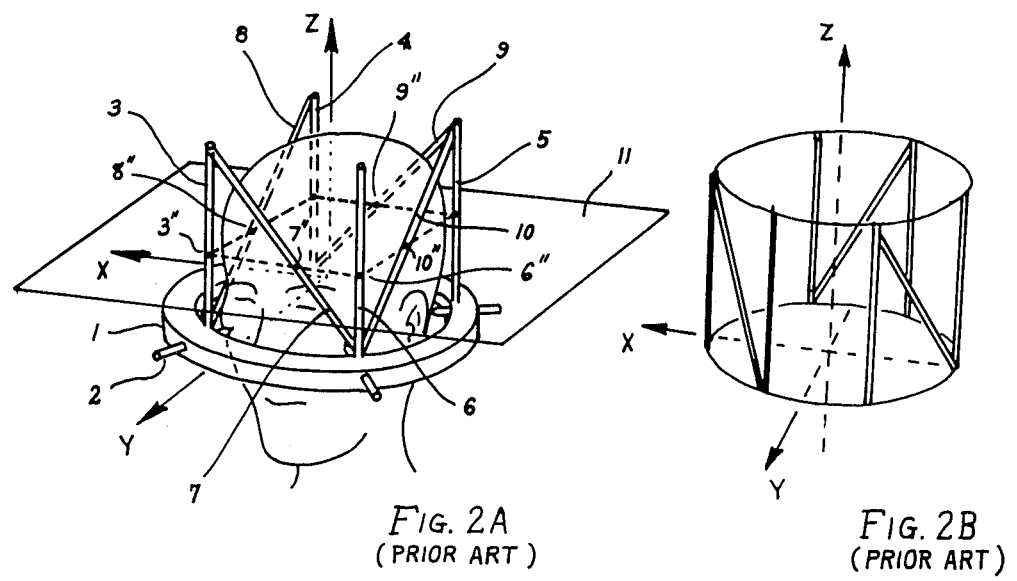
FIG. 2A
(PRIOR ART)
FIG. 2B
(PRIOR ART)
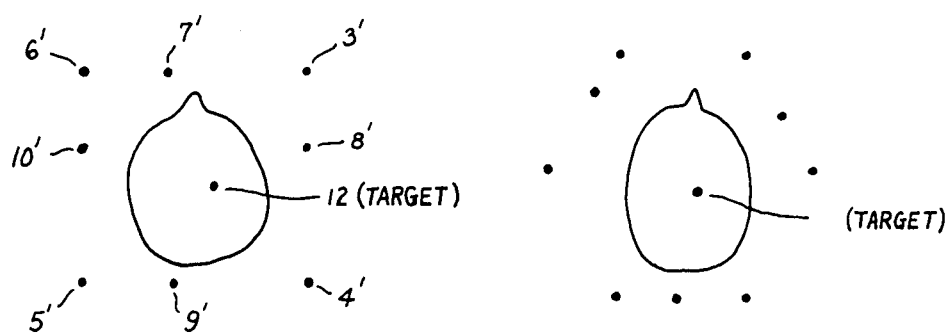
FIG. 3A
(PRIOR ART)
FIG. 3B
(PRIOR ART)

MEANS FOR LOCALIZING TARGET COORDINATES IN A BODY RELATIVE TO A GUIDANCE SYSTEM REFERENCE FRAME IN ANY ARBITRARY PLANE AS VIEWED BY A TOMOGRAPHIC IMAGE THROUGH THE BODY

BACKGROUND OF THE INVENTION

Over the past few years, instruments have been developed which enable a target point seen from a CAT (Computerized Axial Tomography) scan slice to be related precisely in space to an instrument or guidance system attached to the body of the patient that is being scanned. Such a system is referred to as a localizer system. Until this present invention, localizer systems have enabled image points to be determined only for axial slices, which are the type that the CAT scan provides. Now, however, the NMR (Nuclear Magnetic Resonance) and PET (Position Emission Tomography) scanners enable scan slices in nearly any arbitrary plane. The present invention is related to determining target coordinates from such arbitrary plane slices.

Preliminary to describing the invention, the definitions of axes and planes will be given. FIG. 1 shows a head and an x,y,z coordinate system superposed. The body axis is the Z-axis, and a planar slice perpendicular to that axis will be referred to as an axial slice or plane. Of course, there is no precise body axis, so these terms refer to axes and planes that are substantially parallel and perpendicular to the body axis, respectively. They may be precisely defined relative to a frame fixed to the body, the axial axis of said frame being approximately parallel to the body axis. The x and y coordinate axes are defined to be perpendicular to the sagital and coronal planes, respectively, as shown in the figure. In the past for CAT scan images, axial plane slices were standard. Now with new generation CAT, NMR, PET and other scanners, slices in the sagital, coronal, or other arbitrary planes can be taken. Note that the sagital plane is one parallel to a plane roughly going through the mid-line of the head (i.e. nose and midway between the ears). The coronal plane is one parallel to a plane that goes through the ears and up over the crown of the head.

The way in which localizers have determined exact coordinates in axial scans to date is illustrated in FIG. 2. Here a head ring 1 is fixed to the skull by screws 2. This provides a rigid apparatus fixed relative to the body. Now, fastened to 1 is a rod system, with rods 3,4,5,6 being essentially parallel to the body axis 2. Between them are diagonals 7,8,9,10. When an essentially axial scan cut 11 is taken through the head, then the rods and diagonals will appear as localizer image spots on the CAT scan image, points 3',4',5',6' and 7',8',9',10' in FIG. 3a. In addition, one might identify a target spot 12 on the CAT image of FIG. 3a. By knowing the proportional distances of the diagonal points from their respective adjacent rods in the image of FIG. 3a, and knowing their actual physical positions on the localizer frame of FIG. 2a, it is possible to calculate the x,y,z positions of each of the diagonal intersection points 7'',8'',9'', and 10'' of the diagonal rods and the scan plane as shown in FIG. 2a. These enable determination of the equation of the plane 11 relative to the x,y,z coordinate system which is related to the frame 1. Also by proportional vector calculations, one can then determine, from the position of the target image 12 in the CAT image, the x,y,z coordinates of the target relative to the frame 1.

Note that one needs at least the (x,y,z) of three of the diagonal intersections 7'',8'',9'', and 10'' to determine the plane 11, so that only 3 diagonals are really required—the fourth may be used as a check or for greater accuracy. Note also that if the frame 1 is clamped parallel to the scan plane 11, then one needs only one diagonal of the four shown to determine the z position of the plane and, thus, the equation of the plane. The version in FIG. 2a is the scheme of the Leksell stereotaxic guide localizer system, in that case using only 2 diagonals and clamping the frame 1 parallel to the scan plane 11.

It is noted peripherally that once the x,y,z coordinates of the target are known relative to the frame 1, then a stereotaxic guidance system can be attached to the frame and an instrument directed to precisely reach the target. This is one of the principal uses of the localizer system i.e., as part of a stereotaxic guide.

FIG. 2b shows another commercially available system, the BRW Brown-Roberts-Wells localizer system. It utilizes six axial rods and three diagonals, thereby determining the three diagonal-plane intersection coordinates, and thus the scan plane, even if the scan plane is not parallel to the frame plane.

FIG. 3b shows a corresponding scan plane image with rod, diagonal, and target image points.

In none of these systems would it be possible to determine x,y,z coordinates of a target if the scan plane were substantially in the sagital or coronal orientations such that the axial rods and their respective diagonals were not cut by the scan plane.

Thus it is an object of this invention to provide a localizer system which can determine target coordinates not only for essentially axial scan cuts, but also for cuts which are substantially parallel to the sagital or coronal planes, or, moreover, for any planar cut through the subject.

DESCRIPTION OF THE FIGURES

FIG. 1 shows the axial, coronal, and sagital planes and associated x,y,z coordinate axis relative to the body.

FIG. 2 (prior art) shows a head frame fixed to the head and axial localizer systems.

FIG. 3 (prior art) shows tomographic images using the localizer of FIG. 2.

DESCRIPTION OF THE INVENTION

The present invention provides a means of localizing a target, i.e. its precise coordinates, relative to a frame which is located in some fixed position to the body being scanned, from a tomographic scan or reconstruction of scan data where the scan plane or cut is in virtually any orientation. This includes the prior cases of axial planes as well as planes that are more nearly parallel to the sagital or coronal planes. As we will see, the invention enables picking-off frame-related coordinates for targets seen in any slice or plane through the subject, parallel to these ideal axial, coronal, or sagital planes or not.

Figure 4:
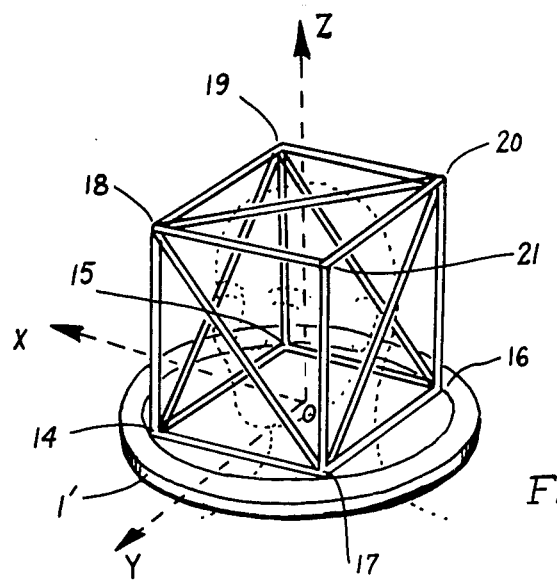
FIG. 4 shows a universal localizer system of parallelapiped geometry.

FIG. 4 illustrates one version of the invention in the application of scanning through the head, although body scanning would be equally applicable. The subject's head is drawn in dashed lines so as not to obscure the features of the invention. Again, we have a frame 1' which has a fixed relation to the subject, most easily accomplished by direct clamping to the head in this example. Attached to 1' is a localizer system consisting of rod elements of such a nature that when the particular scan method is applied, and a tomographic slice is imaged, then the localizer rod intersections with the scan plane appear as localizer spots on the image. For instance, the rods may be made of carbon fiber for CAT scanning, filled with solutions for NMR scanning, or filled with radioactive sources for PET scanning. The localizer system has a fixed relationship to the head frame 1' and thus can be related to a set of coordinate axes (x,y,z) and their origin 0 defined relative to the frame 1'. The axial scheme of prior art involved the axial rods 14–18, 15–19, 16–20, 17–21, (where we designate the rod by the pair of numbers in the figure which specify its end points) and the diagonals 17–18, 14–19, 16–19, 17–20. The diagonals may be oriented differently from what is shown in the specific example of FIG. 4 and accomplish the same effect. For example, they may go from points 14 to 21, 15 to 18, 15 to 20, or 16 to 21 or any combination of these pairs. They need not go exactly through the end points of the rods as shown, but may be offset, or displaced parallel, or at different angles. They need only be arranged so that when the scan plane cuts the localizer as shown in FIG. 2a, then from the image points of the intersection of the plane with the rods and the diagonals one can calculate the x,y,z position of each of the intersection points relative to the frame 1' fixed to the patient.

The novel and new aspect of the embodiment in FIG. 4 is the presence of new rods and a new diagonal which enable determining targets for other than nearly axial planar cuts. The rods 17–14, 14–15, 15–16, 16–17 at the base of the localizer, and 18–21, 18–19, 19–20, 20–21 at the top are oriented in a plane which is perpendicular to the axial rods, that is in the axial plane relative to the frame 1'. The new diagonal 18–20 is also in the axial plane, i.e., perpendicular to the axial direction.

Figure 5A:
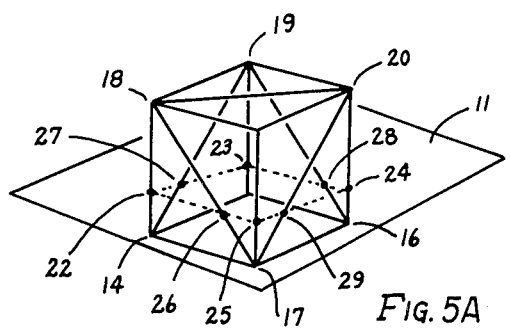
FIG. 5 shows a variety of tomographic planes cutting the localizer of FIG. 4.
Figure 5B:
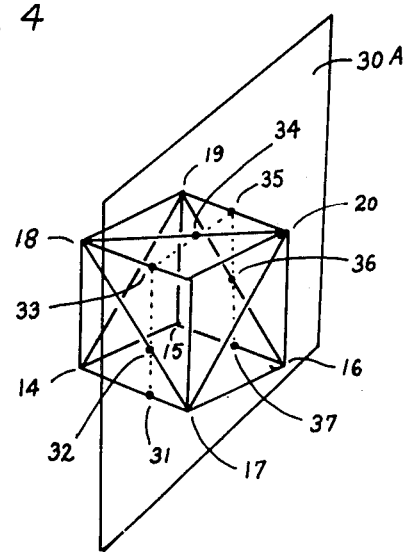
Figure 5C:
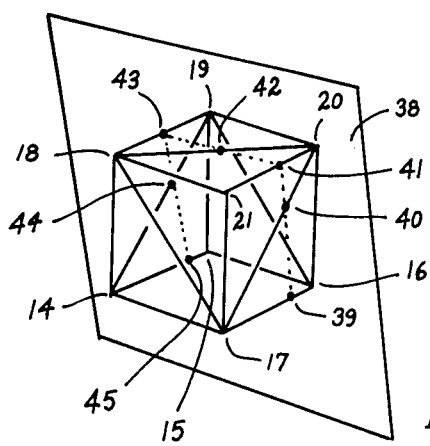
Figures 6A, 6B, 6C:
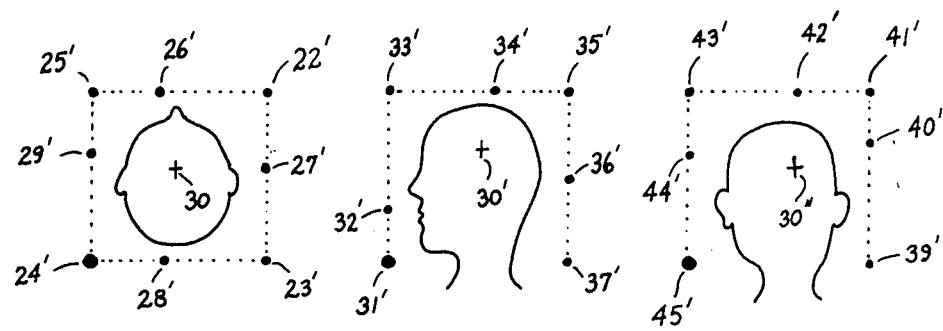
FIG. 6 shows the images in the planes described in FIG. 5.

These new rod structures make possible that sagital and coronal slices or reconstructions will have localizer image spots from which target coordinates from the slice images can be determined, as illustrated in FIGS. 5 and 6. First consider the axial plane cut of prior art, shown in FIG. 5a. Note, we will refer herein as axial planes, planes which are essentially in the axial plane, but may be tilted somewhat from it. The ideal axial plane we can consider as perpendicular to the z-axis of the frame 1'. Plane 11 intersects the four axial localizer rods at points 22, 23, 24, 25 and their connecting diagonals at points 26, 27, 28, and 29. Their images are shown as points on the axial cut image in FIG. 6a, designated as 22', 23',24', 25' and 26', 27',28',29', respectively. A target 30 inside the body is seen on the image also. The proportional distance of 29' from 25' and 24' for instance enable the x,y,z coordinates of point 29 to be calculated relative to the reference frame 1'. The same is true for diagonal points 26,27, and 28. Thus, from any three of these coordinates, the plane 11 can be calculated, and from the relative distances of target image 30 from the rest of the localizer image points in FIG. 6a, the (x,y,z) coordinates of the real target in the body relative to frame 1' coordinate axis can also be calculated.

Now consider the nearly sagital plane 30 as shown in FIG. 5b through the localizer and body. It intersects the new rods at the points 31,33,35, 37. The diagonals are cut at 32,34,36. The image on the sagital plane is shown in FIG. 6b. The image points are 31',32',33',34',35',36',37', and the target image is 30A. Again from these image points, the target coordinates can be calculated relative to the frame 1'. It is only because of the presence of the new rods which are not parallel to the axial direction, that the images 31',33',35',  and 37' are gotten; and because of the new diagonal 18–20 that image 34' is gotten. These are essential to calculating coordinates of the points 32,34,36 and thus to calculating the plane 30 relative to frame 1'. From this, one can calculate the coordinates of target 30' relative to 1'.

FIGS. 5C and 6C show the similar situation for the nearly coronal cut 38 which intersects the rods and diagonals at 39,40,41,42,43,44,45, giving coronal image points 39',40',41',42',43',44',45'. Also shown is a target image 30''. Again, the new non-axial rods at the base and top of the localizer and the new top diagonal enable these images to be seen and thus enable the target associated with image 30'' to be determined in space relative to frame 1'.

The embodiment of the invention shown in FIG. 4 can be considered a right parallelapiped with localizer rods placed on the edges, and the diagonal rods placed on the diagonals between the corners. At least four axial rods parallel to axial edges of the parallelapiped and three associated diagonals not parallel to the four axial rods and each in a plane parallel to one of the axial sides of the parallelapiped are required to give enough localizer image points to fully determine a plane cut which is nearly axial and intersects these elements. Similarly, one must have at least 4 localizer rods, two at the bottom and two at the top (14–17, 15–16, 18–21, and 19–20) parallel to the edges of the parallelapiped which are perpendicular to the axial edges of the parallelapiped, and at least 3 diagonals (17–18, 18–20, and 16–19) which are parallel to the plane defined by pairs of these nonaxial rods to obtain enough image points in a nearly sagital planar cut to calculate the target coordinates of a target image seen on the sagital image. Additionally, to make such a target determination from a nearly coronal planar cut, one needs the additional four rods 14–15, 18–19, 17–16, 20–21 which are perpendicular to the axial direction and parallel to the edges of the parallelapiped in the direction perpendicular to the ideal coronal plane, and the diagonals 17–20, 18–20, and 14–19 which are parallel to planes defined by pairs of these parallel coronal rods, to obtain the sufficient number of coronal images seen in FIG. 6c.

Figure 7:
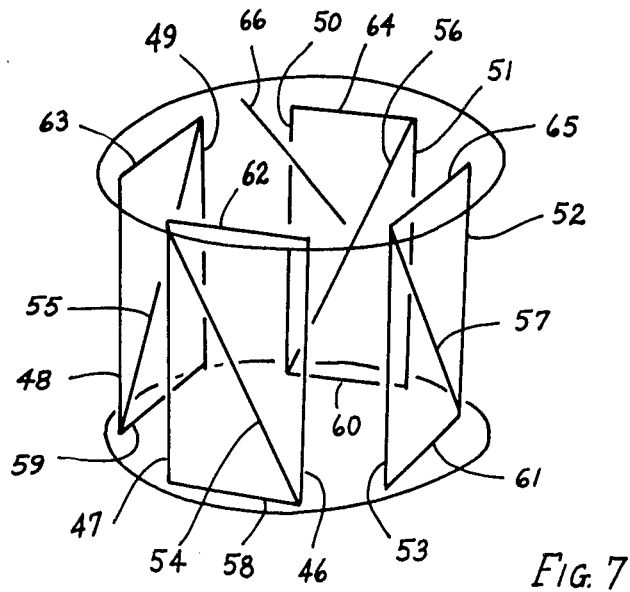
FIG. 7 shows another version of the universal localizer system with separated axial rods.

It is noted that the parallelapiped need not be a cube; its edges on orthogonal axes may have different lengths. Although it is conveniently a right parallelapiped, oblique ones could also be devised to work as a localizer. The diagonal elements need not connect to the corners of the parallelapiped, but need only be in some known geometric relation to the rods so that intersection point coordinates can be calculated. Other variants of the scheme are possible as shown in FIG. 7, where the axial rods of the parallelapiped are replaced by 8 axial rods 46 through 53 with associated four diagonals 54 through 57 (only 3 diagonals are necessary to determine an arbitrary axial plane cut). Also, bottom rods 58 to 61 and top rods 62 to 65 and top diagonal 66 function the same as for the parallelapiped.

There are means of knowing which plane you are imaging from the nature, order, size, or orientation of the rod or diagonal images. For example, in FIG. 6, the rod images 24′,31′, and 45′ are made larger by making corresponding thicker rod elements in the localizer system. This then indexes the rod images so that one knows the orientation of the slice for any of the three types of cuts. Furthermore, by using different sectional shapes or sizes of the rods or diagonals, one can recognize uniquely the sagital versus coronal cuts or the parity of the image that is being viewed. Thus, a unique identification of the plane and its orientation, for any plane in a full 3-dimensions, is possible.

Figure 8:
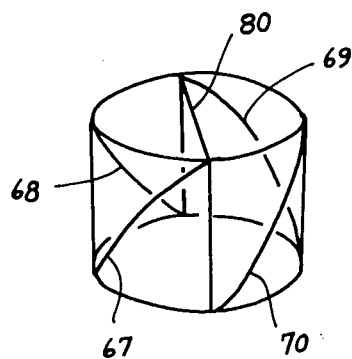
FIG. 8 shows a helical localizer system.

In general, the localizer need not have straight line rod or diagonal elements, but well-defined curved elements could replace them. One example is shown in FIG. 8 where the diagonals are segments of a helix, 67 to 70, and the upper and lower rods are replaced by circular arc elements. Upper diagonal 80 is as it was before, as are the straight axial rods. Of course, the upper diagonal 80 may also be replaced by a curved or spiral element as well. Image points could be reconstructed using solid geometry and polar relationships to derive the frame based coordinates for the plane slice intersection points with these various elements. What is required are elements of the localizer, like those of FIG. 4, which lie in planes essentially parallel to the axial plane so that sagital or coronal cuts will intersect these elements to give index marks on the image. It is the presence of these elements together with the top diagonal element which is different from all previous localizers and is unique to this invention.

We note again in general for the examples given that if the head frame 1′ is clamped so that axial cuts are parallel to it, then fewer localizer elements are needed to define the plane of a slice and to determine target coordinates. Still, for coronal or sagital cuts, the presence of some localizer diagonal on the top, which is parallel to the axial plane, i.e. perpendicular to the axial direction, is essential to defining precisely the plane of a cut which is approximately, but not quite exactly, in the coronal or sagital planes.

Another comment of note is that the present invention applies not only to imaging systems that explicitly derive the sagital or coronal or axial cuts, but also those which reconstruct a series of axial cuts to generate an entire volumetric image, and then project out planar images subsequently in any arbitrary plane such as sagital or coronal. That is, if one takes a series of axial cuts using the localizer of FIG. 4, then the new rod and diagonal elements which are parallel to the axial plane will appear in certain axial cuts. Later, when all axial cuts are reassembled in a computer, mathematical projections in other planes will intersect the rods and diagonals and show them as point spots. Other imaging techniques using time-swept scanning (as in certain NMR techniques) will similarly produce spot reconstructed image intersections with the invention's localizer rods and diagonals.

Figure 9:
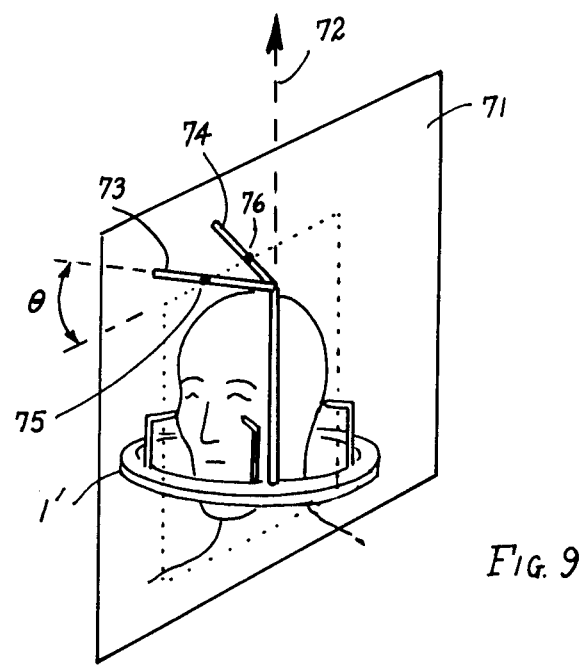
FIG. 9 shows a simple localizer for non-axial planar slices when the slice plane orientation relative to the frame is known.

Finally, if the image cut is known to be parallel to the axial axis of the localizer system and frame and if the cut has a known angular orientation to said axial axis, then only two non-axial elements (i.e., transverse elements) need be present to define the position of the plane and to calculate the target coordinates. FIG. 9 shows an example, where plane slice 71 is parallel to axial 72 and is oriented with a known angle $\theta$ relative to a rod element 73. Another non-parallel diagonal element 74 is in a known geometric orientation to rod element 73. Here the plane 71 is fully defined by its position relative to the elements 73 and 74. This is determined by noting the relationship of the image points of intersections 75 and 76 on the slice image. Again the elements 73 and 74 lie perpendicular to the axial axis and allow determination of the sagital slice 71, analogous to the similar non-axial elements of the more general case illustrated in FIG. 4.

Having described in detail various embodiments of my invention, it will be apparent to those skilled in the art that numerous modifications can be made therein without departing from the scope of the invention as defined in the following claims.

What I claim and desire to secure by Letters Patent of the United States is:

1. A localizer system that can be placed in a fixed spacial relationship to a body to be scanned by a scanning apparatus that produces scan images in which target images of a physical target in the body can be seen and can be related to specific coordinates of the physical target in the body relative to said localizer system, said localizer system comprising:

A. a localizer having an axial axis, said localizer comprising:
   (i) at least twelve rod elements which lie on the edges of a right parallelapiped which can be defined mathematically in space relative to said localizer system;
   (ii) at least three side diagonal rod elements which are not parallel to any of said rod elements, but each of said side diagonal elements being parallel to at least one of the four planar axial sides of said parallelapiped which are parallel to said axial axis;
   (iii) at least one top diagonal rod element which lies in a plane that is perpendicular to said axial axis and which is not parallel to any of the edges of said parallelapiped;

B. means for placing said localizer in a fixed relationship to the body to be scanned with the localizer axial axis being substantially parallel to the axis of the body to be scanned so that any reconstructed planar slice from a scan will lie in an arbitrary plane relative to the axes of said parallelapiped and intersect at least four of said rod elements and at least three of said diagonal elements and a slice image therefrom will contain identifiable image marks corresponding to the intersection of the planar slice with said elements, and so that if a target image is present in the slice image, the coordinates of the target in the body associated with said target image can be calculated.

* * * * *